(12) United States Patent
Oberländer et al.

(10) Patent No.: US 8,945,002 B2
(45) Date of Patent: Feb. 3, 2015

(54) SEAL FOR CLOSING-OFF AN ACCESS INSTRUMENT INTO A BODY

(75) Inventors: Martin Oberländer, Engen (DE); Kevin Pilz, Tuttlingen (DE); Michael Sauer, Tuttlingen (DE); Sebastian Wagner, Bretten (DE)

(73) Assignee: Karl Storz GmbH & Co. KG (DE)

( * ) Notice: Subject to any disclaimer, the term of this patent is extended or adjusted under 35 U.S.C. 154(b) by 537 days.

(21) Appl. No.: 12/762,117

(22) Filed: Apr. 16, 2010

(65) Prior Publication Data

US 2010/0268035 A1 Oct. 21, 2010

(30) Foreign Application Priority Data

Apr. 17, 2009 (DE) .......................... 10 2009 018 639

(51) Int. Cl.
*A61B 1/32* (2006.01)
*A61B 17/34* (2006.01)

(52) U.S. Cl.
CPC ..... *A61B 17/3462* (2013.01); *A61B 2017/3445* (2013.01); *A61B 2017/3449* (2013.01); *A61B 2017/3466* (2013.01); *A61B 2017/3484* (2013.01)
USPC .......................................................... 600/204

(58) Field of Classification Search
USPC .................................. 600/201–217; 227/636
See application file for complete search history.

(56) References Cited

U.S. PATENT DOCUMENTS

| | | | | |
|---|---|---|---|---|
| 6,033,426 A | * | 3/2000 | Kaji ............................... | 606/213 |
| 6,551,270 B1 | | 4/2003 | Bimbo et al. | |
| 7,311,704 B2 | * | 12/2007 | Paul et al. ....................... | 606/41 |
| 7,347,853 B2 | * | 3/2008 | DiFiore et al. ................. | 604/537 |
| D619,716 S | * | 7/2010 | Wagner ......................... | D24/147 |
| D665,905 S | * | 8/2012 | Oberlaender et al. ........ | D24/135 |
| 8,403,840 B2 | * | 3/2013 | Wagner et al. ................. | 600/210 |
| 2002/0038077 A1 | * | 3/2002 | de la Torre et al. ........... | 600/203 |
| 2002/0185825 A1 | * | 12/2002 | Miyamoto et al. ............ | 277/636 |
| 2003/0144577 A1 | | 7/2003 | Bacher et al. | |
| 2005/0267332 A1 | * | 12/2005 | Paul et al. ...................... | 600/127 |
| 2006/0247500 A1 | * | 11/2006 | Voegele et al. ................ | 600/208 |
| 2007/0026953 A1 | * | 2/2007 | Ohshita et al. ................ | 464/175 |
| 2007/0210535 A1 | * | 9/2007 | Inagaki et al. ................. | 277/635 |
| 2007/0225081 A1 | * | 9/2007 | Toriumi ......................... | 464/175 |
| 2008/0025519 A1 | | 1/2008 | Yu et al. | |

(Continued)

FOREIGN PATENT DOCUMENTS

DE 102009014525 A1 9/2010
EP 0043218 A1 1/1982

(Continued)

OTHER PUBLICATIONS

European Search Report; EP 10 16 0035; Jul. 23, 2010; 4 pages.

*Primary Examiner* — Ellen C Hammond
*Assistant Examiner* — Jacqueline Johanas
(74) *Attorney, Agent, or Firm* — St. Onge Steward Johnston & Reens LLC

(57) ABSTRACT

A seal (10) is used for closing-off a proximal-side access port of an access instrument into a body. It has a cap (12) having a wall (14) covering the access port and a circumferential collar (16), which can be put over an edge of the access port. At least two approximately circular-segment-shaped openings are present in the wall (14), wherein a flexible dome sits on each opening and, on the proximal side, has, compared to the circular-segment-shaped openings, a smaller entry port (26, 28).

20 Claims, 8 Drawing Sheets

(56) References Cited

U.S. PATENT DOCUMENTS

| | | |
|---|---|---|
| 2008/0161826 A1 | 7/2008 | Guiraudon |
| 2008/0255519 A1 | 10/2008 | Piskun et al. |
| 2008/0281161 A1* | 11/2008 | Albrecht et al. ............. 600/206 |
| 2010/0030032 A1* | 2/2010 | Voegele et al. ............. 600/210 |
| 2010/0063452 A1* | 3/2010 | Edelman et al. ............. 604/175 |
| 2010/0234689 A1 | 9/2010 | Wagner et al. |
| 2010/0312063 A1* | 12/2010 | Hess et al. ................. 600/204 |
| 2011/0021878 A1* | 1/2011 | Racenet et al. ............. 600/206 |
| 2011/0144444 A1* | 6/2011 | Sakai et al. ................ 600/206 |

FOREIGN PATENT DOCUMENTS

| | | |
|---|---|---|
| EP | 1314392 A1 | 5/2003 |
| WO | 2008015566 A2 | 2/2008 |
| WO | 2009035663 A2 | 3/2009 |

* cited by examiner

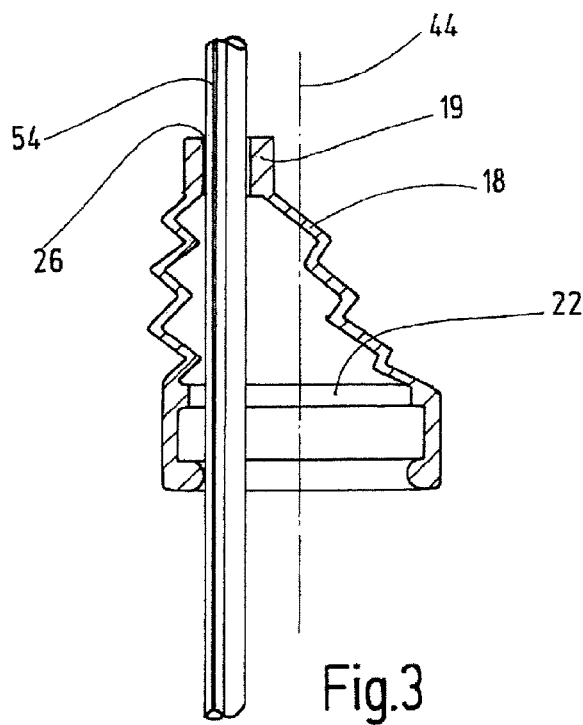
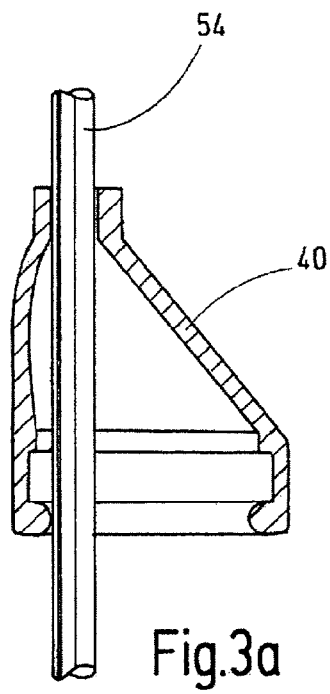
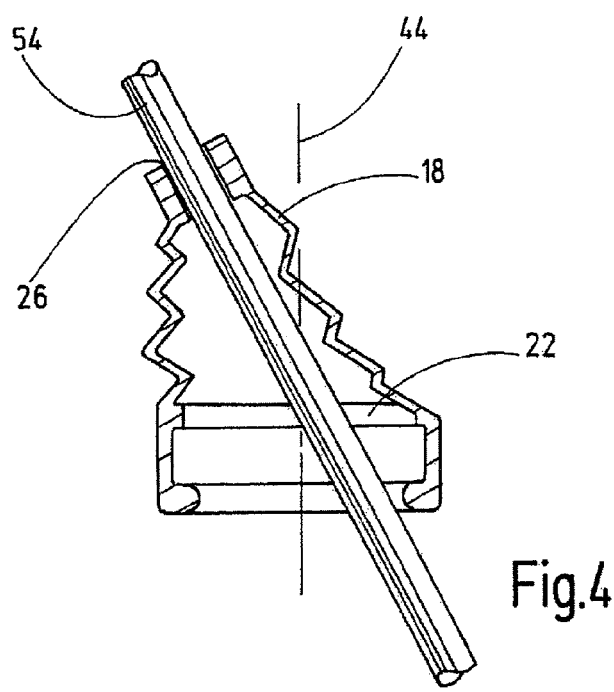

SEAL FOR CLOSING-OFF AN ACCESS INSTRUMENT INTO A BODY

BACKGROUND OF THE INVENTION

The invention relates to a seal for closing-off a proximal-side access port of an access instrument.

Widely available, minimally invasive surgery has introduced obtaining access to an inner cavity of a body by means of an access instrument. Trocars are such access instruments, the trocar sleeve of which pierces the abdominal wall in e.g. laparoscopy. So that this is brought about as atraumatically as possible, a small incision, usually with a length of 1-1.5 cm, is firstly introduced into the skin, the trocar with a pointed trocar pin is placed onto said incision and then pushed through the abdominal wall. The trocar sleeve is removed again after the intervention and the incision is closed. After a certain amount of time, nothing relating to the surgery can be seen on the outside, bar a small scar in the skin. There are certain limits to the diameter of the trocar sleeve, which are in the region of approximately 15 mm.

However, since minimally invasive surgery in e.g. the internal abdominal cavity requires that a number of instruments are guided through, it has become conventional to place a plurality of trocars on e.g. the abdominal wall in such an intervention, with 3 to 4 trocars by all means being common.

In a development of this access technology, the applicant has developed an access instrument into a body, which instrument allows the creation of a significantly larger access port, particularly when the access instrument is inserted through the navel, and therefore a plurality of instruments can be guided through this access instrument at the same time. That is to say, only a single access instrument is necessary, with the single, relatively large access port thereof allowing simultaneous guiding-through of a plurality of instruments (Single Port Access).

The body of such an access instrument is made up of, for example, two parts, with each part having a distal body section, which merges into a proximal body section protruding outwardly from the central longitudinal axis. The distal body sections can be assembled in a first position to form a distal body with laterally protruding proximal body sections. The two assembled distal body sections together virtually form a trocar sleeve and can be pushed through the abdominal wall in laparoscopy, as described above. Here, the diameter can be of the order of conventional trocar sleeves. Subsequently, the two subsidiary body sections protruding laterally from the body are assembled by swivelling or mutual approaching to form a proximal hollow body, the outer proximal edge of which constituting the access port of the access instrument.

During this swivelling, the two distal body sections sticking in the body and originally folded together are moved apart and swivelled. As a result of an appropriate embodiment of the transition region between the distal and proximal body sections, this swivelling can widen the port in the abdominal wall a little further. The two proximal body sections can delimit a port on their proximal edge, which port has a diameter of a plurality of centimeters.

This affords the possibility of simultaneously inserting a plurality of instruments into the body through such a single access instrument.

More detailed refinements of such an access instrument are described in more detail and explained in the German patent application by the applicant with the official reference number 10 2009 014 525.7, dated 13 Mar. 2009, and so, the content of this application is inserted into the present application by reference.

If there is a desire to seal such an access instrument in the proximal direction, a seal has to be placed thereon. In laparoscopic surgery an insufflation gas is supplied through the access instrument in order to inflate the abdominal wall and enlarge the internal cavity. Such a seal is provided to prevent the gas from escaping.

Thus, the subject matter of the present invention relates to such a seal for closing-off a proximal access port of an access instrument into a body.

EP 1 314 392 B1 discloses a seal for an endoscope, in which different seals are inserted into ports, a plurality of said ports being provided in the wall of a rigid cap that can be screwed onto the end of an endoscope. All of these ports are circular and the ports serve to seal, in a gas-tight fashion with respect to the outside, a shaft of an instrument pushed through this seal. In some seals, the proximal-side port, through which the shaft of an instrument should be pushed through in a sealing fashion, is smaller than the port in the cap into which the seal has been inserted. In order to allow a certain amount of lateral or tilting movement of the instrument inserted through the seal, the body of said instrument is designed as bellows.

It is therefore an object of the present invention to create a seal for closing-off a proximal-side access port of an access instrument into a body, which simultaneously allows the guiding of a plurality of instruments through the seal and simultaneously allows moveable handling, i.e. to-and-fro movement and tilting, of the guided-through instruments in a region which is as large as possible.

SUMMARY OF THE INVENTION

According to the invention, the object is achieved by a seal that has a cap having a wall covering the access port of the access instrument and a circumferential collar, which can be put over the edge of the access port, wherein at least two approximately circular-segment-shaped openings are present in the wall, wherein a flexible dome sits on each opening and, on the proximal side, has, compared to the circular-segment-shaped port, a smaller entry port for the sealed insertion of a shaft of an instrument. In certain embodiments, each of the entry ports are monolithic with said corresponding upstanding flexible dome and said cap.

These measures now have various advantages.

Since the seal has a cap with a wall covering the entire access port of the access instrument, the entire port can be sealed without further additional components such as sealing caps, union nuts or the like. The circumferential collar, which is put over an edge of the access port, ensures a secure and sealing seat of the seal in this access port. Here, the wall can span ports with a diameter in the region of a plurality of centimeters, up to the order of 10 cm.

The provision of at least two circular-segment-shaped openings, on which the flexible domes are seated, provides relatively large ports in the region of the wall that afford an operating range that is as large as possible for an instrument pushed through the flexible dome. In the process, this circular-segment-shaped opening is many times larger than the cross-sectional area of the shaft-like instrument pushed through the flexible dome. Thus, there is, compared to the circular-segment-shaped opening, a smaller port on the proximal side of the flexible dome, which port butts against the shaft of the instrument in a sealing fashion. The flexible dome can be designed as a sack-like formation, which has a relatively small diameter at the proximal end and expands at the distal end to take the shape of the circular-segment-shaped opening.

That is to say that the instrument can be inserted into the flexible dome and through the relatively small port in a sealing fashion on the proximal side. However, the desired operating range is made possible by the significantly larger circular-segment-shaped opening in the wall at the base of the flexible dome. Operating range means that, for example, the shaft can be moved to-and-fro in the circumferential direction or in the direction of a secant along the circular-segment-shaped opening, and can also perform extreme tilting movements, i.e. the shaft can be guided through the seal at an extreme angle. The flexible dome can follow these movements.

Since at least two of such circular-segment-shaped openings are available, this results in a relatively large operating range for two instruments, which range lies at least in the region of 90° for each instrument as seen in the circumferential movement direction, and, moreover, the aforementioned tilting movements can be carried out at the same time.

That is to say, this large operating range allows the surgeon to move the distal end of an instrument pushed through this seal in a very large space in the body cavity. That is to say, the surgeon can handle a plurality of instruments in a very large operating range in the body, despite there being a single access through the abdominal wall (Single Port Access).

This constitutes a considerable development in minimally invasive surgery, which in the end leads to significantly fewer incisions into the body being required for performing minimally invasive surgery.

In a refinement of the invention, a flexible dome is designed as a dome-like bellows.

The advantage of the refinement as bellows is that this geometry is particularly suitable for allowing the required movements of an instrument inserted into the flexible dome, i.e. lateral movements or tilting movements.

In a further refinement of the invention, the bellows taper in a Christmas-tree-like fashion, as seen across a secant extending along the circular-segment-shaped port.

This Christmas-tree-like bellows structure affords both lateral displacement movements of the bellows and extreme tilting movements, without a very bulky design being required above the seal. Despite the extreme displacement and tilting movements, it is always ensured that the instrument can be guided through the bellows in a gas-tight fashion and so no insufflation gas escapes and has to be reintroduced into the body cavity as a result.

In a further refinement of the invention, all bellows have at least three folds.

It was found that three folds can achieve outstanding freedom of movement using conventional materials, e.g. silicone rubber materials. This geometry in conjunction with the selected material does not require excessive force to deform the bellows and moreover allows the restoration force of the material to put the bellows into its desired alignment when no instrument is inserted and has been displaced or tilted.

In a further refinement of the invention, the flexible domes are arranged in a mirror-imaged fashion with respect to a diameter of the wall.

The advantage of this measure is that two opposing dome-like structures are available, which then permit a maximally large operating range but nevertheless allow sufficient material to be left standing between the domes to ensure sufficient mechanical rigidness of the seal. It should be noted that, unlike the prior art mentioned at the outset, the seal does not seal only a relatively small through-hole, but a relatively large access port of the access instrument, which port has a diameter extending over a plurality of centimeters.

In a further refinement of the invention, at least one further port is formed in the wall between the flexible domes.

The significant advantage of this measure now is that further instruments can be guided through this region, which instruments do not require this operating range, i.e. do not require a dome, but merely require a through-hole. Such ports include, for example, ports for gas connections or the like.

As mentioned previously, the diametric, mirror-imaged arrangement of the two domes affords a relatively large region of wall material therebetween, and so further ports can also be provided in this region between the domes, without having a negative influence on the mechanical stability of the seal.

In a further refinement, an access for a further instrument, in particular an optical system, is created in a first further port.

The advantage of this measure is that, for example, an optical system can be introduced which registers the entire internal cavity such that the manipulations performed by the moveable instruments guided through the domes then can be observed by means of this unmoving optical system.

In previously conventional minimally invasive surgery, three trocars would have to have been placed for this, one for the optical system and two for the instruments, with the trocars for the instruments not even permitting said operating ranges.

This should be considered to be a particular advantage of the seal according to the invention.

In a further refinement of the invention, a gas connection is inserted into a second further port.

The advantage of this measure is that the insufflation gas can also additionally be guided through the seal in this region.

Trocars usually have a trocar housing with a connection protruding laterally therefrom, to which the insufflation gas can be connected. The aforementioned advantageous refinement of the seal thus affords guiding the necessary instruments, the optical system and the gas connection through the seal and so the actual access instrument no longer needs to have such connections and can have a correspondingly simple design, possibly as a single-use disposable part.

In a further refinement of the invention, a further port has a reducing bush inserted therein, which bush has, on the proximal side, a port with a smaller diameter than this port.

The advantage of this measure is that a certain basic size of a further port can be provided. If significantly thinner shafts are intended to be guided there-through, a reducing bush is used, and the additional instrument, for example an optical system, is then guided through said bush.

In a further refinement of the invention, a clamp is integrated into the cap.

The advantage of this measure is that the clamp can be used to affix the seal particularly tightly on the edge of the access port.

In a further refinement of the invention, the clamp is designed as a diametric strap, claws at the end thereof butting against the edge of the access instrument.

In doing so, it is advantageous to embed the diametric strap directly into the material of the seal as well, for example to cast it directly as well when moulding the seal in the case of a design as a silicone seal. In this region, which can be situated between the two flexible domes opposing one another in a mirror-imaged fashion, the strap then forms an additional reinforcement and so this web between the domes can have an extremely narrow design since this strap contributes to the stability. This then affords the possibility of designing the operating range at the base of the domes such that it is maximized in terms of area.

In a further refinement of the invention, a slit seal is arranged in a proximal-side collar of a flexible dome.

The advantage of this measure is that the proximal-side ends of the domes are sealed by the slit seals if no instrument has been pushed therethrough or if, for example, an instrument has only been pushed through one of the at least two domes.

In a further refinement of the invention, slit seals are arranged on the distal side on the further ports.

This measure has the same effect as mentioned above, i.e. these slit seals seal the further ports either if the latter are not needed, i.e. no instruments have been inserted therethrough, or while an instrument is being removed and replaced by another.

Seen overall, all access ports or through-holes thus are correspondingly sealed and so there is a gas-tight closure even if no instrument has been inserted therein.

Said closure for example opens the possibility of, for preparing minimally invasive surgery, firstly placing the seal on the access port of the access instrument by putting the collar thereover and supplying insufflation gas through the seal and into the body via a gas connection. Then, the instruments can be guided through the flexible domes bit-by-bit and actual surgery can commence.

In a further refinement of the invention, the clamp is designed such that subsidiary body sections of an edge surrounding the access port of the access instrument can be held together.

As mentioned initially, an advantageous field of application for the seal is an access instrument made up of two body sections that can be folded. The collar of the seal placed over the edge already has a certain holding function, i.e. it holds together these two subsidiary body sections proximally protruding from the body.

In the case of extremely large ports or great enlargement of the body openings, and in the case of extremely stiff or solid abdominal walls, very strong forces act in the direction of separation or splaying of the folded-up proximal subsidiary body sections.

The provision of a clamp in the cap can now additionally hold together these subsidiary body sections by means of said clamp. This constitutes a particularly advantageous refinement in the field of application of access instruments made up of subsidiary body sections.

In a further refinement of the invention, at least one protrusion protrudes from said cap, said protrusion can be gripped and facilitates a mounting of said cap on a rim of said access port.

This measure has the advantage that the cap can be gripped at the protrusion, maybe by hand or by a tool. Pulling the protrusion causes an expanding of the cap which facilitates the mounting of the cap at the rim of the access port.

In a further refinement of the invention, several protrusions protrude circumferentially distributed from said cap.

This measure has the advantage that the cap can be gripped on different or on several places simultaneously and can be expanded. This facilitates the placing of the cap remarkably.

In a further refinement of the invention the at least one protrusion protruded readily outwardly from a lower end of the collar.

This measure has the advantage that the mounting of the circumferential collar is particularly facilitated. Only the collar needs to be expanded without expanding the remaining parts of the seal, in particular the wall covering the access port.

In a further refinement of the invention the at least one protrusion is designed as a flap.

This measure has the advantage that such a flap can be easily gripped between two fingers of a hand and the flap can be pulled. The collar can be expanded to such an extent that it can be moved easily over the rim of the access port opening. In the refinement with several flaps, it is possible to pull on two or more diametrically opposed flaps.

It is understood that the aforementioned features and the features yet to be explained below can be used not only in the specified combinations but also in other combinations or on their own, without departing from the scope of the present invention.

The invention will be described in more detail and explained on the basis of a few selected exemplary embodiments in conjunction with the appended drawings, in which:

FIG. 3 shows an illustration comparable to FIG. 2, in which a shaft of an instrument has been inserted into dome-like bellows and displaced laterally from a normal alignment;

FIG. 3a shows an illustration comparable to FIG. 3, in which the flexible dome is designed as a smooth-walled, flexible, sack-like body;

FIG. 4 shows an illustration comparable to FIG. 3, which shows tilting of the shaft held in the dome-like bellows;

A first embodiment of a seal as shown in FIGS. 1-6 is denoted in its entirety by reference sign 10.

The seal 10 consists of an elastic silicone rubber material and is manufactured by an injection-moulding process.

Figure 2:
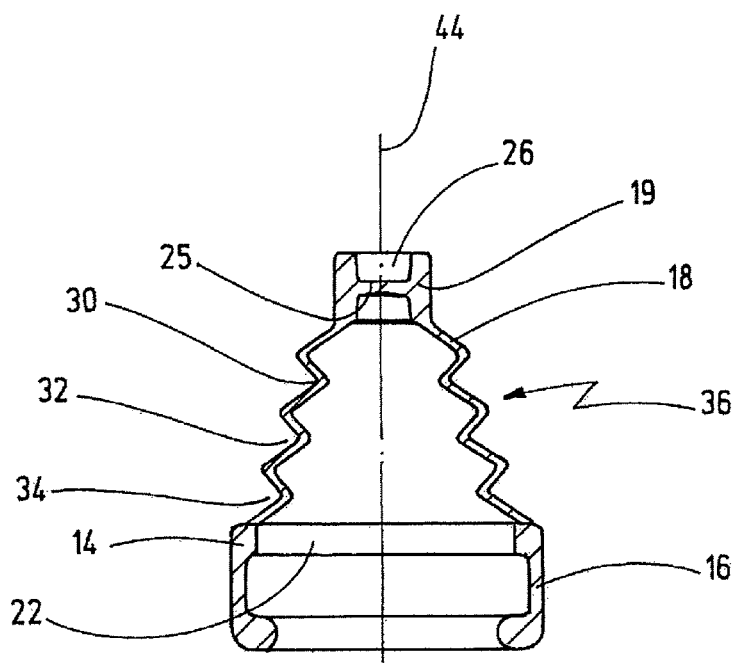
FIG. 2 shows a section along the line II-II in FIG. 1.

The seal 10 has a first section in the form of a cap 12, which has a disc-like, approximately planar wall 14, with a collar 16 protruding circumferentially therefrom in the proximal direction. Two dome-like bellows 18 and 20 rise in the proximal direction from the wall 14. The sectional illustration in FIG. 2 shows that, seen from distal to proximal, the dome-like bellows 18 on this side have Christmas-tree-like tapering 36 and three folds 30, 32 and 34. At the proximal end, there is a cylindrical stud 19, which encircles an entry port 26. A slit seal 25 is arranged in the stud 19.

In the following text, bellow-like domes are described; however, the latter can also be sack-like, flexible domes enabling the same movements as described in conjunction with the dome-like bellows 18 and 20.

Figure 1:
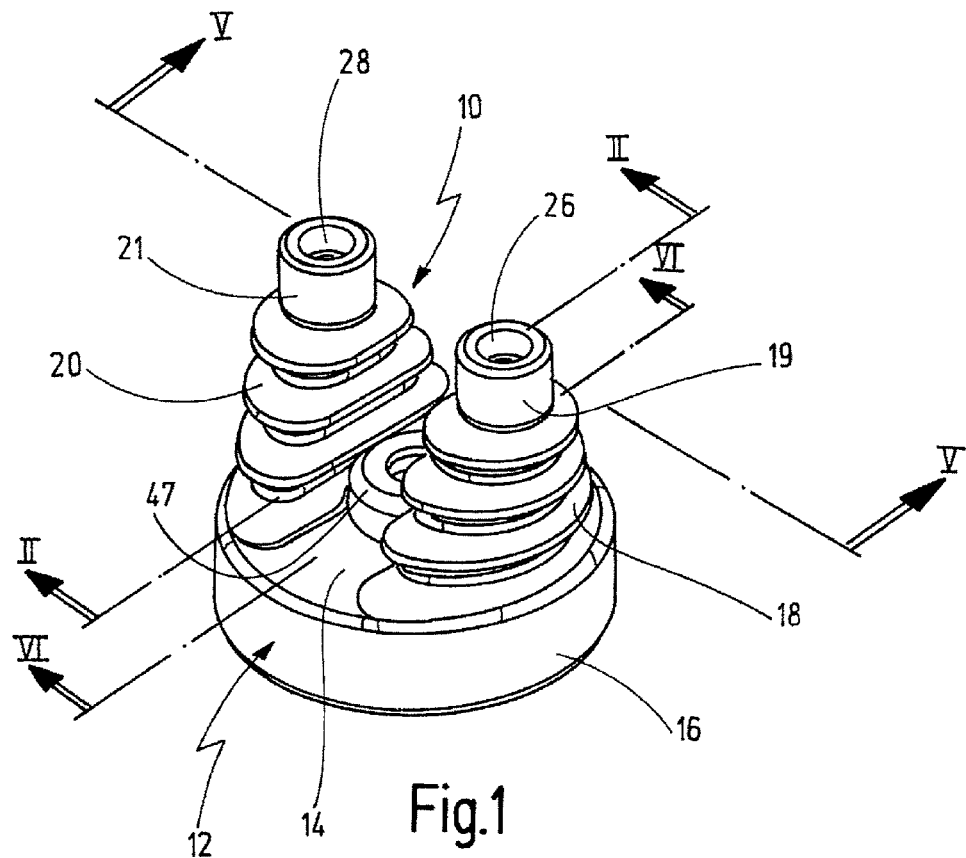
FIG. 1 shows a perspective view of a first exemplary embodiment of a seal according to the invention.
Figure 6:
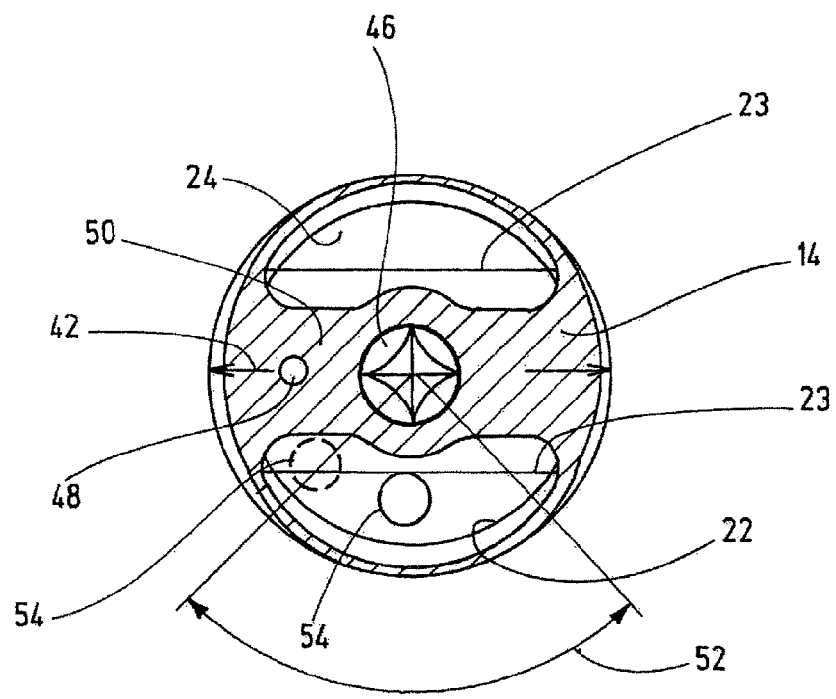
FIG. 6 shows a section along the line VI-VI in FIG. 1.

The perspective illustration in FIG. 1 shows that the dome-like bellows 20 situated opposite the dome-like bellows 18 also have the same design, just mirror-imaged in respect thereof, with the plane of the mirror extending along a diameter 42 as shown in FIG. 6. FIG. 6 shows a plan view of the wall 14 from proximal to distal. This sectional image shows that two approximately circular-segment-shaped openings 22, 24 are cut out of the wall 14. These two openings 22, 24 as it were form the open base of the dome-like bellows 18 and 20.

The two bellows 18 and 20 rise over the openings 22 and 24.

Figure 5:
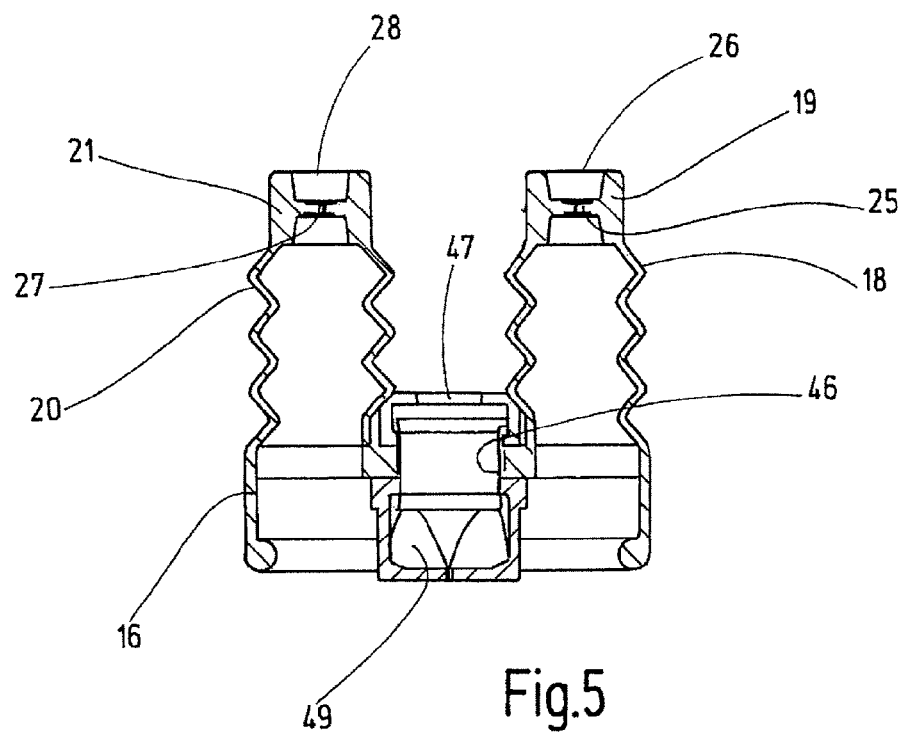
FIG. 5 shows a section along the line V-V in FIG. 1.

The sectional illustration in FIG. 5 shows that the two bellows 18 and 20 are arranged at a radial distance from one another. The illustration in FIG. 6 shows that therebetween there is a material web 50, which ensures sufficient mechanical stability of the wall 14. FIG. 6 shows that, in the web 50, there is a first further port 46, which, as shown in FIG. 5, is closed-off on the distal side by a cross-slit seal 49.

Figure 7:
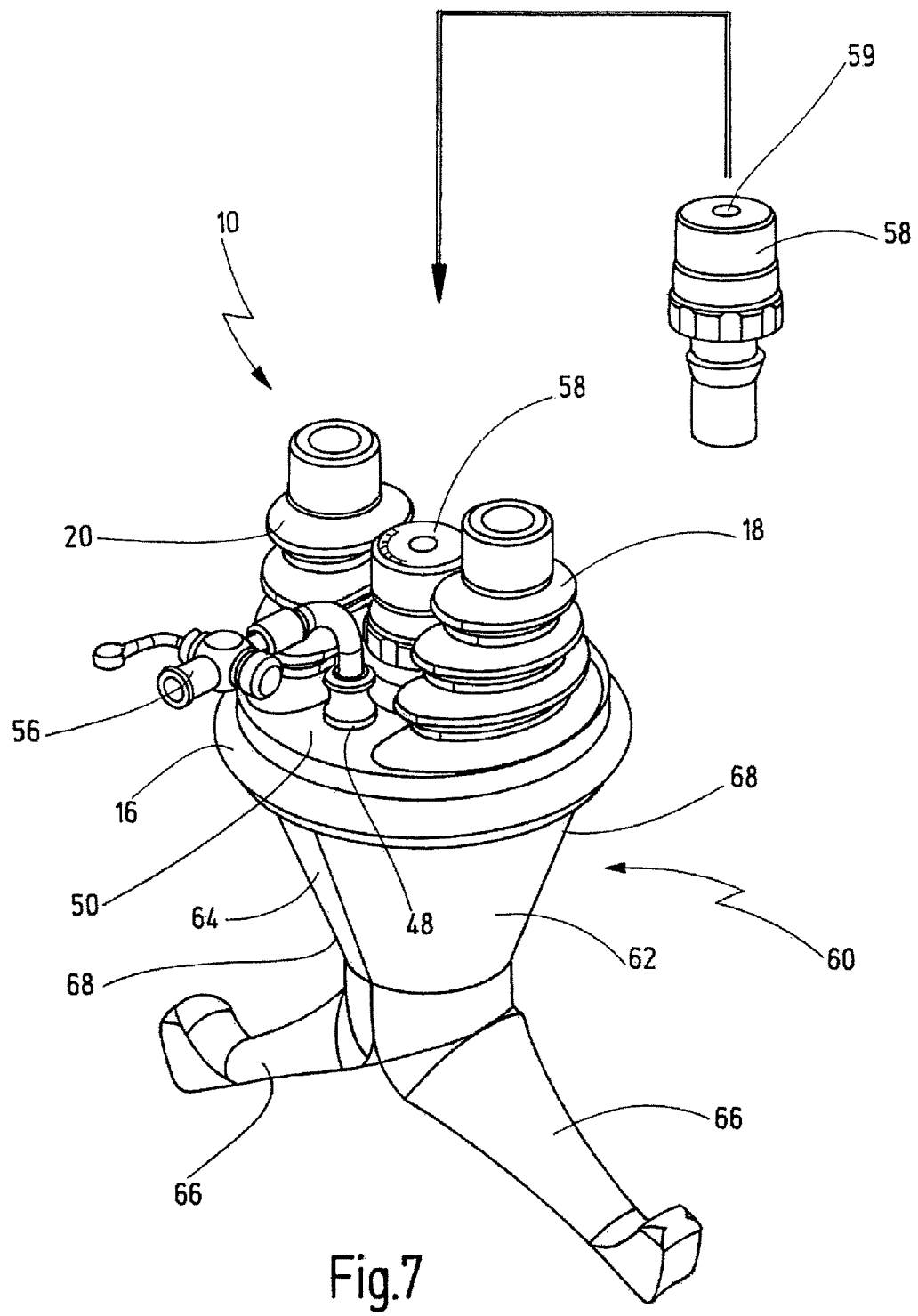
FIG. 7 shows a perspective view of an assembly of the seal according to the invention, as in FIG. 1, and an access instrument, wherein a gas connection and, moreover, a reducing bush are additionally inserted into the seal.

A significantly smaller, second further port 48 is used to insert a gas connection 56 therein, as shown in FIG. 7.

A cylindrical plug-in seal 47 determining a certain maximum insertion port diameter is inserted into the proximal side of the first further port 46.

A particular advantage when handling the seal 10 is intended to be described in conjunction with FIGS. 1-6.

FIG. 3 illustrates how a shaft 54 of a surgical instrument is pushed through the dome-like bellows 18. The shaft 54 is usually aligned with the central longitudinal axis 44 of the dome, as illustrated in FIG. 2. Due to the bellows-like design, the shaft 54, for example, can now be moved from the alignment with the central longitudinal axis 44 and to the right-hand side or left-hand side thereof, as illustrated in FIG. 3.

This is possible, on the one hand, due to the design as bellows and, on the other hand, because there is the approximately circular-segment-shaped or kidney-shaped opening 22 shown in FIG. 6. It is obvious that these movements are also permitted by sack-like domes without folds. The sacks only have to be designed such that the positions illustrated in FIG. 3 and FIG. 4 are likewise possible.

The position of the shaft 54 in FIG. 6 denoted by a solid circle would correspond to the alignment thereof if the shaft were inserted into the bellows 18 as illustrated in FIG. 2.

The position of the shaft 54 indicated by the dashed line in FIG. 6 corresponds to the position illustrated in FIG. 3, i.e. a position of maximum displacement to the left. The length of the displacement path corresponds to the length of a secant 23 of the circular-segment-shaped opening 22.

FIG. 3a shows a further embodiment in which a flexible dome 40 is formed from a sack-like, smooth-walled elastic plastic.

The material is so flexible that there can be the same movements as described in conjunction with the dome-like bellows.

FIG. 4 shows that the shaft 54 can be not only displaced to-and-fro, but also tilted relatively extremely. FIG. 4 in conjunction with FIG. 6 shows that, in this position, the shaft 54 can be tilted so far until it butts against the (in the illustration in FIG. 6) right-hand end of the opening 22.

The combination of the movements as illustrated in FIG. 3 and FIG. 4 thus result in a significant operating range 52, as illustrated in FIG. 6. It is obvious that a distal end of the shaft can reach a very large space in the body of a patient due to this design.

Naturally, this also holds true for a further shaft inserted into the other bellows 20, and for the design as a dome 40 as illustrated in FIG. 3a.

FIG. 7 illustrates a situation in which the seal 10 has been placed onto an access instrument 60.

The access instrument 60 is made up of two body sections 62 and 64.

Each of these body sections 62 and 64 has a distal body section 66 and a proximal body section 68 protruding laterally therefrom. FIG. 7 illustrates a situation in which the two proximal body sections 68 are assembled to form a conical hollow body, which is widening relatively strongly in the proximal direction.

Figure 8:
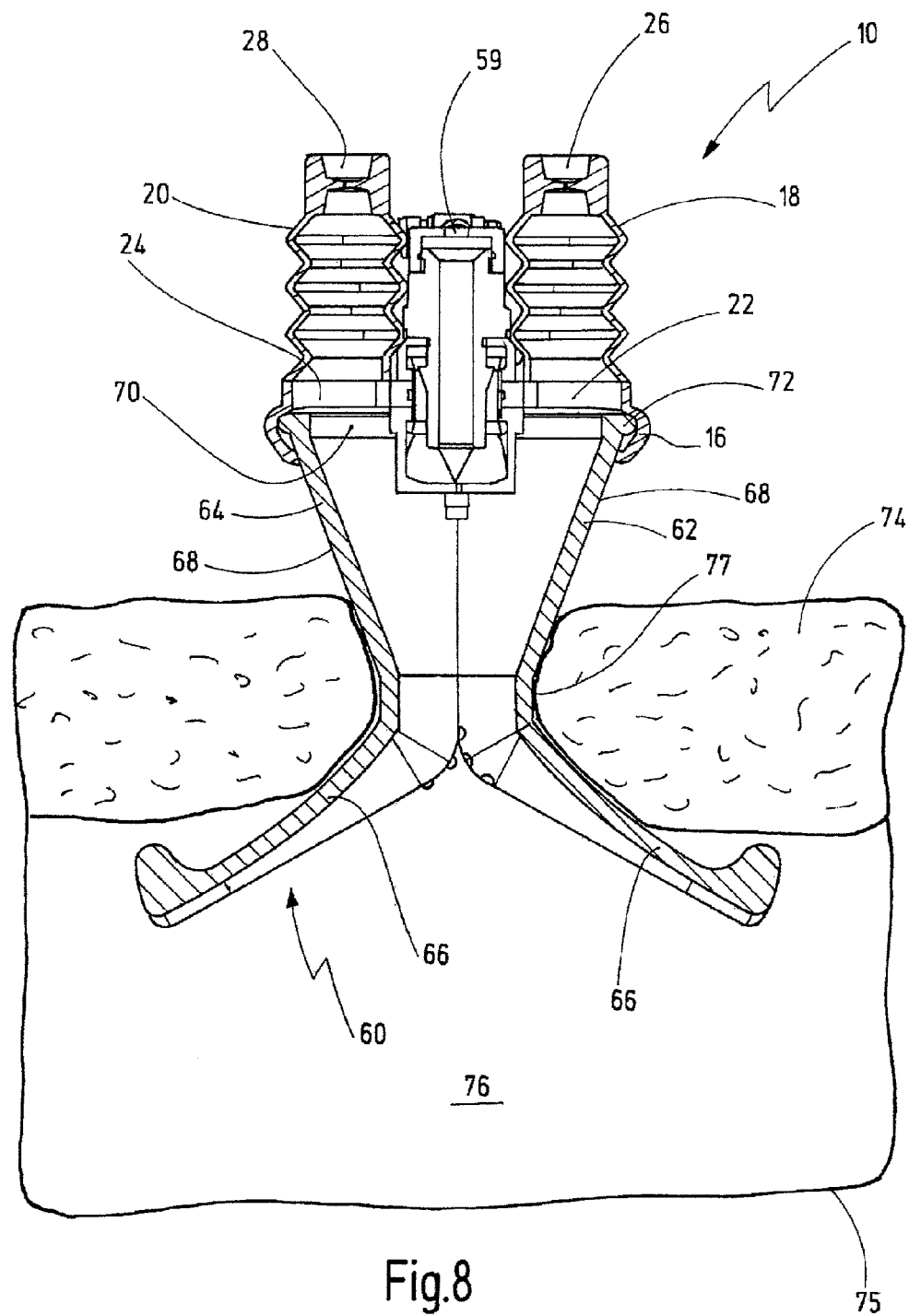
FIG. 8 shows a vertical section through the assembly of FIG. 7, with this illustrating how this assembly is inserted into an abdominal wall of a human body.

The sectional illustration in FIG. 8 shows that this proximal hollow body surrounds a relatively large access port 70, on the upper edge 72 of which the seal 10 has been placed. Here, the collar 16 of the seal 10 is placed over the edge 72 of the access port 70 of the access instrument 60. The design and selection of elastic material are such that the edge 72 is closed-off in a gas-tight fashion by the seal 10 after the collar 16 has been placed over said edge. FIG. 7 shows that a gas connection 56 has been inserted into the second further port 48 and, moreover, a reducing bush 58 has been inserted into the cylindrical plug-in seal 47 shown in FIG. 1. This reducing bush 58 has a smaller port 59 and so an instrument with a correspondingly thin shaft can be guided through said port.

The perspective illustration in FIG. 7 in conjunction with FIG. 8 shows that insufflation gas can be supplied via the gas connection 56 via the seal 10 or the wall 14 thereof, shafts 54 of corresponding surgical instruments can be guided through via the dome-like bellows 18 and 20 and a further instrument, for example an optical system, can be guided through the reducing bush 58. All instruments guided through the seal 10 are guided through the proximal hollow body, made up of the two body sections 68, and reach in the internal cavity, e.g. the abdominal cavity 76, of a body 75 after the access instrument 60 has been inserted in said body.

The access instrument 60 is guided into the body 75, or through the abdominal wall 74, such that, at first, it is not provided with the seal 10 and the two distal body sections 66 are assembled to form a relatively narrow body, as described in the German patent application of the applicant cited at the outset. The two distal body sections 66 lying next to one another are driven through the abdominal wall 74 in this assembled state. Subsequently, the two body sections 62 and 64 are swivelled against each other or tilted such that the two proximal body sections 68 come to rest against one another and the distal subsidiary body sections 66 already situated in the interior of the body are spread as illustrated in FIG. 8, i.e. nearly abut on the lower side of the abdominal wall 74. The seal 10 can now be put thereon in this assembled state by placing the collar 16 of the seal over the edge 72.

In the transition from the aforementioned position, in which the distal body sections 66 lie next to one another, to the spread position illustrated in FIG. 8, the port 77 in the abdominal wall 74 is also enlarged and so significant restoring forces can act on the two spread body sections 66 and could again cause spreading of the proximal subsidiary body sections 62. The placed-on collar 16 of the seal 10 counteracts this spreading movement. However, since a gas-tight closure should also be ensured along the separation line of the two body sections 62 and 64, particularly in the region lying outside of the body, it is necessary for these two parts to be held securely against one another.

Figure 9:
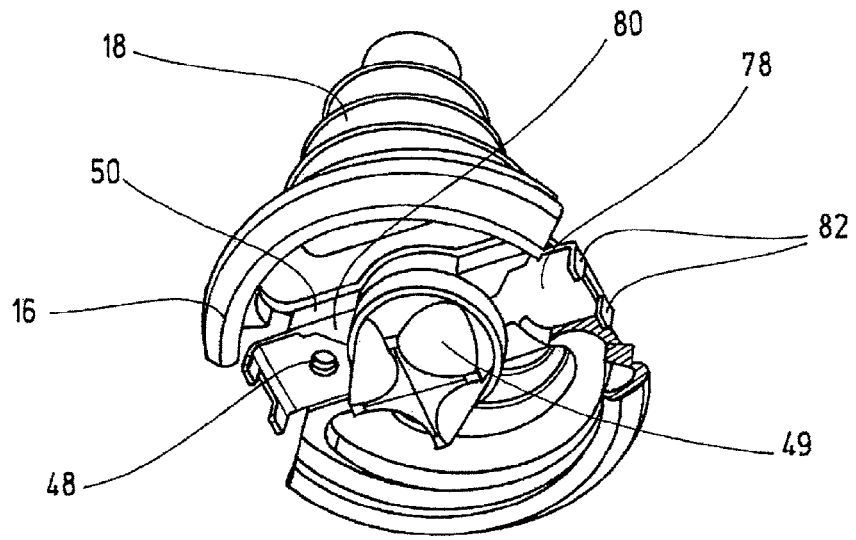
FIG. 9 shows a perspective, partly cut open, view of the distal end of an exemplary embodiment of a seal according to the invention with an integrated clamp.
Figure 10:
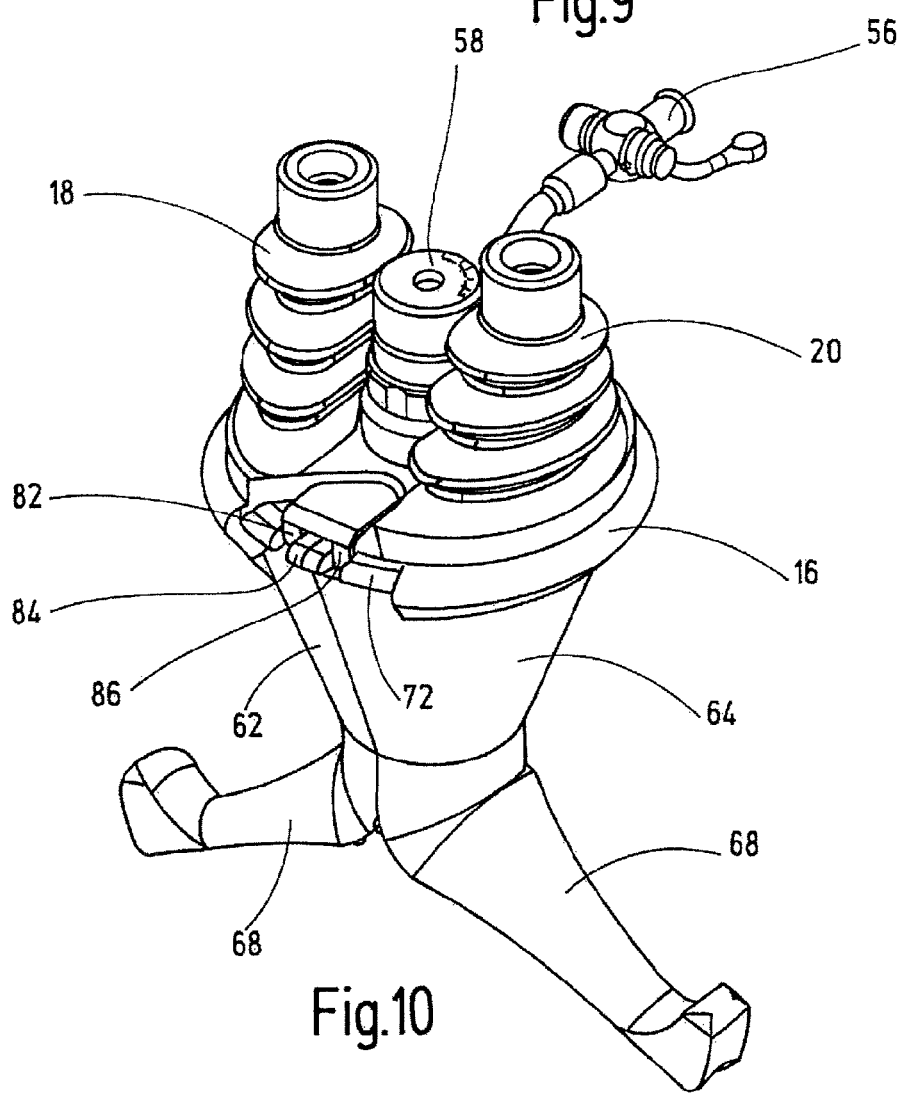
FIG. 10 shows a perspective illustration in which the seal of FIG. 9 is placed onto an access instrument made up of two subsidiary halves and, in doing so, holds these two subsidiary halves together using the clamp.

For this, in the exemplary embodiment of a seal according to the invention illustrated in FIG. 9 and FIG. 10, a clamp 78 is integrated into the wall 14. The clamp 78 has a diametrically extending strap 80, to be precise in the region of the web 50 between the two dome-like bellows 18 and 20. The illustration in FIG. 9 shows that the second further port 48 for the gas connection is also formed in the web, as is the first further port for the cylindrical plug-in seal 47, which cannot be seen here because it is covered by the distal-side cross-slit seal 49. The strap, which can, for example, be made of metal and also can be worked in or moulded in during the production of the seal, ensures increased rigidity of the seal in the region of the wall 14.

At its end, the strap 80 has claws 82, which, as can be seen particularly in FIG. 10, engage in grooves 86 on both sides of humps 84 on the edge 72. The overlapping claws 82 then hold the two subsidiary body sections 62 and 64 tightly against one other and thus also in a gas-tight fashion.

Hence, the seal does not only bring about the actual sealing objective, but also, additionally, a holding function as a support for the two subsidiary body sections 62 and 64 of the access instrument 60.

After minimally invasive surgery has been performed through the seal 10, the latter can again be removed from the access instrument by removing the placed-on collar 16. Once the seal 10 has been removed, the access instrument can again be folded over, and so the two distal subsidiary body sections 66, rising in the body, lie against one another and can then be removed through the abdominal wall 74.

Figure 11:
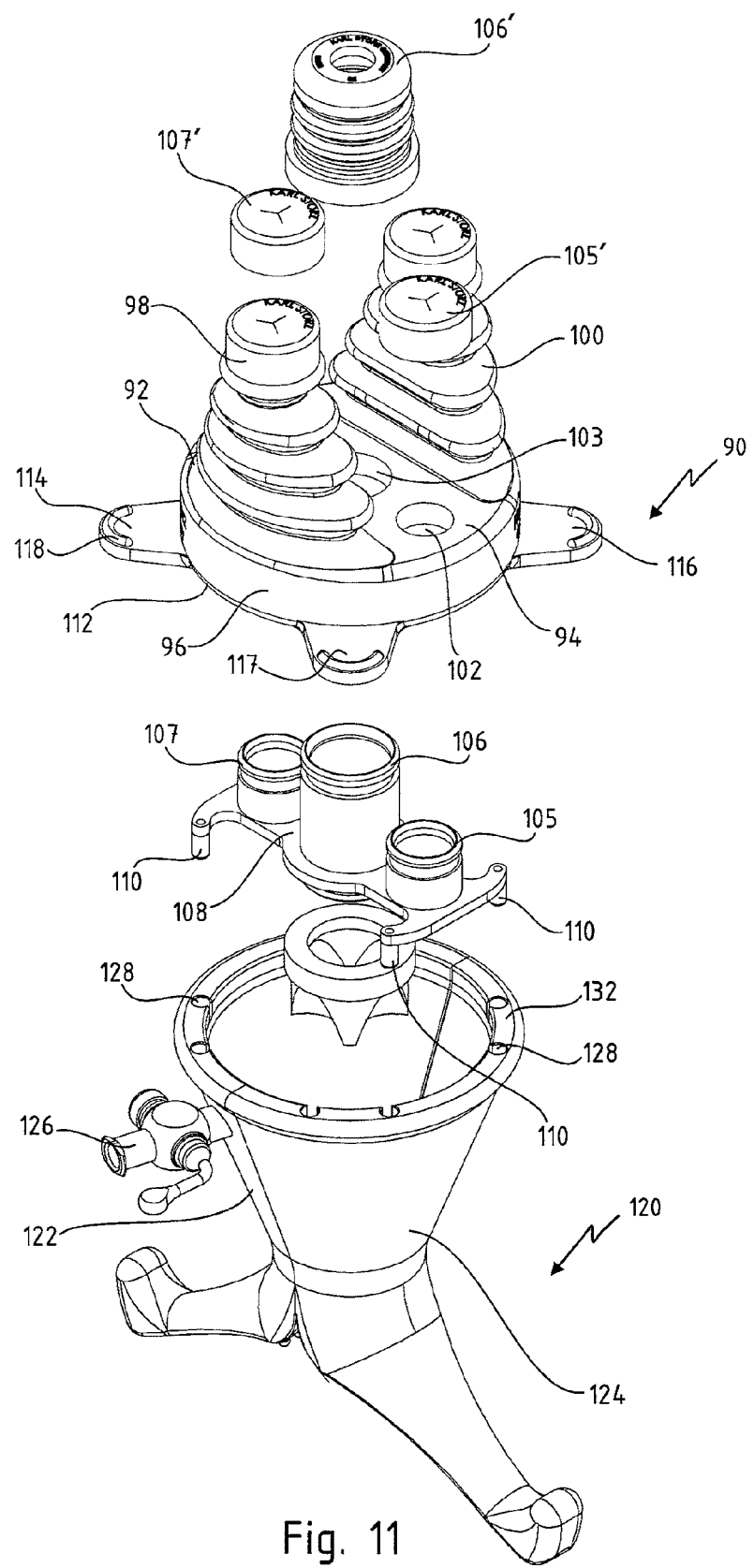
FIG. 11 shows a perspective exploding view of a second exemplary embodiment of a seal.
Figure 12:
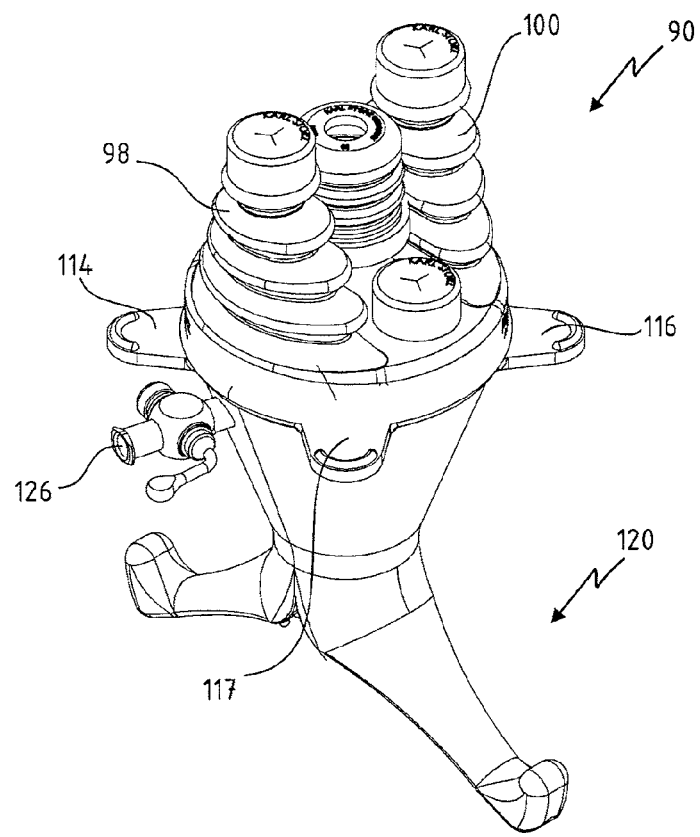
FIG. 12 shows the seal of FIG. 12 in assembled condition and mounted on an access instrument.
Figure 13:
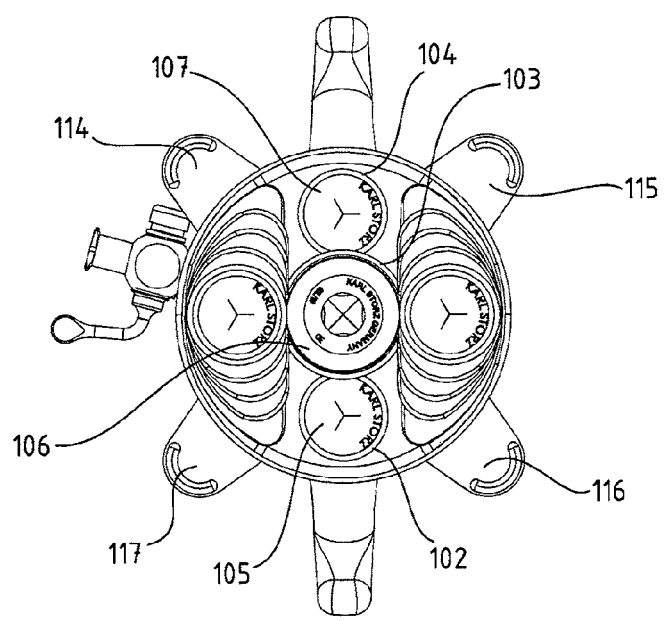
FIG. 13 shows a top view onto the seal from FIG. 12.

A further embodiment of a seal according to the invention is shown in FIGS. 11 through 13 and is entirely designated with reference number 90.

The seal 90 is made of a similar expandable material as the above-described seal 10.

The seal 90 also has a cap 92 having a disk-like flat wall 94. From the circumferential rim, in the illustration of FIG. 11, a circumferential collar 96 extends downwardly.

Two dome-like bellows 98 and 100 arise from the wall 94 as it was described above in connection with seal 10.

In the area between the two upstanding bellows 98 and 100 three further openings are provided.

In these three further openings 102, 103, 104 three seals 105, 106, 107 are inserted. It can be seen in particular from FIG. 11 that three tube section-like bodies of the seals 105, 106, 107 are mounted on a clamp 108. Pins 110 project from the underside of clamp 108.

These pins 110 can be inserted into recesses 128 provided at the upper rim 132 of an access instrument 120 which is assembled from two body sections 122 and 124.

Therefore, clamp 108 has the same purpose as clamp 78, i.e. to hold the two body sections 122 and 124 together in that assembly condition.

From the lower end 112 of collar 96 four outwardly directed, circumferentially equally distributed flaps 114, 115, 116 and 117 protrude. These flaps 114 through 117 are protrusions, via which the seal 90 can be gripped and be somewhat expanded for mounting purposes, i.e. by pulling at the flaps.

This facilitates to mount the collar 96 over the rim 132 of the access instrument 120.

The outer ends of the flaps 114 through 117 are provided with bulges which prevent a sliding-off of a finger which has gripped a flap. Respective bulges can be provided at the underside of the flap. During mounting the clamp 108 is set onto the upper rim 132 and following to this cap 92 is mounted in that the three upstanding seals 105, 106, 107 are pushed through the respective openings 103, 104 and 105.

For facilitating the setting of the collar 96, it can be pulled at the flaps 114 to 117 in radially outwardly directed manner.

The mounting can also be done in that the cap 92 and the clamp 108 are assembled and then this assembly is mounted on the rim 132 whatever is more suitable for the operating people. Onto the three seals 105, 106, 107 pushed through the three openings 102, 103, 104 respective sealing caps 105', 106' and 107' are mounted.

In FIGS. 12 and 13 the final mounted condition is shown.

It can be seen that with this embodiment, a Luer connection 106 projects from the body section 122. Via the Luer connection 126, media, which may be gaseous or liquid can be fed to the access instrument 120.

After a use, the cap can be easily withdrawn from the access instrument 120 in that one pulls at one or more of the flaps 114 through 117 and moves the cap away from the access instrument 120.

Here, the use of the seals 10 and 90 was described in conjunction with a specially designed access instrument 60 and 120, but it is obvious that the seal can also be placed onto a different access instrument with an appropriate diameter. What is important is that this single seal can bring about a large-area seal of this relatively large access port and that a multiplicity of manipulations can be carried out through this seal, namely the surgical procedures through the bellows, the insufflation flow through the gas connection and visual observation through an optical system inserted centrally into the seal.

The principle of the Single Port Access has now been developed to the end of being able to carry out all manipulations through a single seal closing-off this Single Port Access.

The invention claimed is:

1. A seal for closing-off a proximal access port of an access instrument into a body, the seal comprising:
    a cap having a wall covering an access port, said wall having a collar which is put over an upper edge of said access port; and
    at least two approximately circular-segment-shaped openings in said wall, said at least two approximately circular-segment-shaped openings each delimited by part of a circle and a secant cutting said circle and each separated from another by a web of material extending between said openings, each of said openings being covered by an upstanding flexible dome, each of said domes has, on a proximal end thereof, an entry port for sealingly inserting a shaft of a medical instrument, each of said entry ports having a smaller size than that circular segment-shaped opening seen along said secant in said wall covered by said dome, each of said upstanding flexible domes has an open base having a cross-section corresponding to the shape of said circular-segmented shaped opening in said wall, and each of said domes tapers to a cylindrical stud at said proximal end encircling one of said ports,
    wherein said web between said at least two circular-segment-shaped openings has a mechanical stability sufficient to avoid a collapsing of the wall when instruments are inserted into said entry ports,
    wherein each of said entry ports are monolithic with said corresponding upstanding flexible dome and said cap.

2. The seal of claim 1, wherein said flexible domes are designed as dome-like bellows.

3. The seal of claim 2, wherein said bellows taper in a Christmas-tree-like fashion, as seen across each secant extending along said circular-segment-shaped openings.

4. The seal of claim 3, wherein said bellows has at least three folds.

5. The seal of claim 1, wherein said flexible domes are arranged in a mirror-imaged fashion with respect to a diameter of said wall.

6. The seal of claim 1, wherein one or more further ports is provided in said wall between said two flexible domes.

7. The seal of claim 6, wherein a first port of the one or more further ports provides an access for a further instrument.

8. The seal of claim 6, wherein a second port of the one or more further ports has a gas connection inserted therein.

9. The seal of claim 6, wherein a further port of the one or more further ports has a reducing brush inserted therein, said brush has on a proximal side a port having a smaller diameter than said further port.

10. The seal of claim 6, wherein slit seals are arranged on said at least one further port.

11. The seal of claim 1, wherein a clamp is integrated into said cap.

12. The seal of claim 11, wherein said clamp is designed such that body sections of the access instrument can be held together via said clamp.

13. The seal of claim 1, wherein a slit seal is arranged in the cylindrical stud of each flexible dome.

14. The seal of claim 1, wherein at least one protrusion protrudes from said cap, said protrusion can be gripped and facilitates a mounting of said cap on a rim of said access port.

15. The seal of claim 14, wherein the at least one protrusion comprises several protrusions which protrude circumferentially and are distributed over said cap.

16. The seal of claim 14, wherein said at least one protrusion protrudes radially outward from a lower end of said collar.

17. The seal of claim 14, wherein said at least one protrusion is designed as a flap.

18. The seal of claim 1, wherein the shaft of the medical instrument inserted into said entry port can be moved along a displacement path corresponding to a length of said secant.

19. An access instrument for insertion into a body comprising:
   a distal body section and a proximal body section protruding laterally therefrom;
   an access port surrounded by the proximal body section, the access port having an upper edge; and
   a seal for closing-off the access port, the seal placed over the upper edge of the access port, the seal comprising:
      a cap having a wall covering the access port, said wall having a collar which is put over the upper edge of said access port, said wall having a clamp integrated into the wall, the clamp having a diametrically extending strap having claws able to overlap an edge of the access port of the access instrument to be sealed by the seal, and
      at least two approximately circular-segment-shaped openings in said wall, said at least two approximately circular-segment-shaped openings each delimited by part of a circle and a secant cutting said circle and each separated from another by a web of material extending between said openings, each of said openings being covered by an upstanding flexible dome, each of said domes has, on a proximal end thereof, an entry port for sealingly inserting a shaft of a medical instrument, each of said entry ports having a smaller size than that circular segment-shaped opening seen along said secant in said wall covered by said dome,
   wherein said web between said at least two circular-segment-shaped openings has a mechanical stability sufficient to avoid a collapsing of the wall when instruments are inserted into said entry ports,
   wherein each of said entry ports are monolithic with said corresponding upstanding flexible dome and said cap.

20. A seal for closing-off a proximal access port of an access instrument into a body, the seal comprising:
   a cap having a wall covering an access port, said wall having a collar which is put over an upper edge of said access port; and
   at least two approximately circular-segment-shaped openings in said wall, said at least two approximately circular-segment-shaped openings each delimited by part of a circle and a secant cutting said circle and each separated from another by a web of material extending between said openings, each of said openings being covered by an upstanding flexible dome, each of said upstanding flexible domes has an open base having a cross-section corresponding to the shape of said circular-segmented shaped opening in the wall, and each of said domes tapers to a cylindrical stud at said proximal end thereof encircling an entry port on each of said domes, said entry ports for sealingly inserting a shaft of a medical instrument, each of said entry ports having a smaller size than that circular segment-shaped opening seen along said secant in said wall covered by said dome,
   wherein said web between said at least two circular-segment-shaped openings has a mechanical stability sufficient to avoid a collapsing of the wall when instruments are inserted into said entry ports,
   wherein a clamp is integrated into said cap and said clamp is designed as a diametric strap, having claws at its opposite ends thereof butting against said access instrument.

* * * * *